United States Patent [19]

Martin et al.

[11] Patent Number: 5,196,438
[45] Date of Patent: Mar. 23, 1993

[54] AMINO ACID DERIVATIVES

[75] Inventors: Joseph A. Martin, Harpenden; Sally Redshaw, Stevenage, both of England

[73] Assignee: Hoffmann-La Roche Inc., Nutley, N.J.

[21] Appl. No.: 615,534

[22] Filed: Nov. 19, 1990

[30] Foreign Application Priority Data

Dec. 11, 1989 [GB] United Kingdom ............... 8927913

[51] Int. Cl.$^5$ ..................... A61K 31/47; C07D 265/30
[52] U.S. Cl. ................................ 514/311; 514/314; 546/164
[58] Field of Search .................. 546/164; 514/314, 311

[56] References Cited

U.S. PATENT DOCUMENTS

| | | | |
|---|---|---|---|
| 3,901,897 | 8/1975 | Hauck et al. | 546/84 |
| 4,123,543 | 10/1978 | Jonsson et al. | 424/274 |
| 4,329,473 | 5/1982 | Almquist et al. | 546/281 |
| 4,470,973 | 9/1984 | Naterajan et al. | 424/177 |
| 4,720,484 | 1/1988 | Vincent et al. | 514/18 |
| 4,812,442 | 3/1989 | Boger et al. | 514/18 |
| 4,863,905 | 9/1989 | Hudspeth et al. | 514/18 |
| 4,965,250 | 10/1990 | Vincent et al. | 514/18 |

FOREIGN PATENT DOCUMENTS

| | | |
|---|---|---|
| 190058 | 8/1986 | European Pat. Off. |
| 230052 | 7/1987 | European Pat. Off. |
| 0230082 | 7/1987 | European Pat. Off. |
| 264106 | 10/1987 | European Pat. Off. |
| 292800 | 5/1988 | European Pat. Off. |
| 282374 | 9/1988 | European Pat. Off. |
| 309841 | 9/1988 | European Pat. Off. |
| 337714 | 4/1989 | European Pat. Off. |
| 346847 | 12/1989 | European Pat. Off. |
| 163437 | 6/1958 | Sweden . |
| 933968 | 8/1963 | United Kingdom . |
| WO88/00939 | 2/1988 | World Int. Prop. O. |

OTHER PUBLICATIONS

Derwent Abstract of EPA 264106 (Apr. 20, 1988).
Derwent Abstract of EPA 292800 (Nov. 30, 1988).
Dewent Abstract of EPA 309841 (Apr. 20, 1989).
Derwent Abstract of EPA 342541 (Nov. 23, 1989).
Derwent Abstract of EPA 346847 (Dec. 20, 1989).
Derwent Abstract of WO88/00939 (Feb. 11, 1988).
Meek et al. "Inhibition of HIV-1 Protease . . . ", *Nature*, 343, 90 (Jan. 4, 1990).
McQuade "A Synthetic HIV-1 Protease Inhibitor . . . ", *Science*, 247, 454 (Jan. 26, 1990).
Dreyer "Inhibition of Human Immunodeficiency Virus 1 . . . ", *Proc. Natl. Acad. Sci.* USA, 86(24), 9752 (1989).
Frey "Lactone Precursor . . . ", *J. Org. Chem.*, 51(25), 4828 (1986).
Jouin, "Synthesis . . . ", *J. Org. Chem.*, 54(3), 617 (1989).
Harris, "Didemnins III", *Tetrahedron*, 44(12), 3489 (1988).
Overton "Effect", *Virology*, 179, 508 (1990).
Roberts, "Rational Design", *Science*, 248, 358 (Apr. 20, 1990).
Kotler, *Proc. Natl. Acad. Sci.* USA, 85, 4185 (1989).
Crumpaker, *N. Engl. J. Med.*, 321, 163 (1989).
Genetic Engineering & Biotechnology Monitor, No. 33, 30 (1991).
Thayer, Chem. Eng. News, 23 Apr. 1990, p. 18.
CA102(19):166520u-1984.
Tetrahedron Letters, 25(51):5899-5902 (1984).

*Primary Examiner*—Marianne M. Cintins
*Assistant Examiner*—Catherine S. Kirby Scalzo
*Attorney, Agent, or Firm*—George M. Gould; George W. Johnston; Alan P. Kass

[57] ABSTRACT

Compounds having the formula

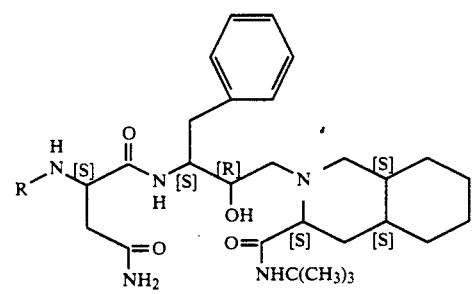

wherein R is benzyloxycarbonyl or 2-quinolylcarbonyl, and their pharmaceutically acceptable acid addition salts inhibit proteases of viral origin and can be used as medicaments for the treatment of prophylaxis of viral infections in mammals, humans or non-humans.

17 Claims, No Drawings

AMINO ACID DERIVATIVES

FIELD OF THE INVENTION

The present invention is concerned with amino acid derivatives.

SUMMARY OF THE INVENTION

The amino acid derivatives provided by the present invention are compounds having the formula

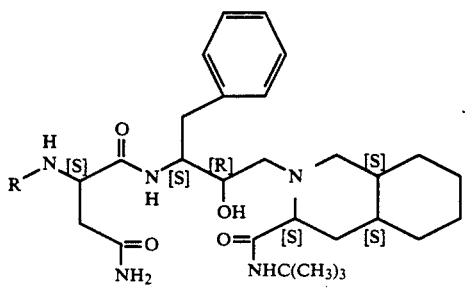

I wherein R is benzyloxycarbonyl or 2-quinolylcarbonyl, and pharmaceutically acceptable acid addition salts thereof.

The compounds of formula I and their pharmaceutically acceptable acid addition salts are novel and possess valuable pharmacological properties. In particular, they inhibit proteases of viral origin and can be used in the prophylaxis or treatment of viral infections, particularly of infections caused by HIV and other retroviruses in mammals, humans or non-humans.

DETAILED DESCRIPTION OF THE INVENTION

The amino acid derivatives provided by the present invention are compounds having the formula

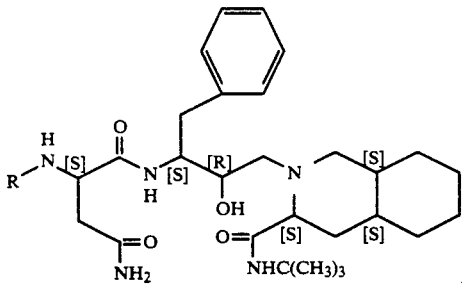

I wherein R is benzyloxycarbonyl or 2-quinolylcarbonyl, and pharmaceutically acceptable acid addition salts thereof.

The compounds of formula I and their pharmaceutically acceptable acid addition salts are novel and possess valuable pharmacological properties. In particular, they inhibit proteases of viral origin and can be used in the prophylaxis or treatment of viral infections, particularly of infections caused by HIV and other retroviruses in mammals, humans or non-humans.

Objects of the present invention are the compounds of formula I and their aforementioned salts, their use as therapeutically active substances, a process for the manufacture of said compounds and salts, intermediates used in said process, medicaments containing said compounds and salts, the use of said compounds and salts in the control or prevention of illnesses, especially in the treatment or prophylaxis of viral infections, and the use of said compounds and salts for the manufacture of medicaments for the treatment or prophylaxis of viral infections.

The pharmaceutically acceptable acid addition salts of the compounds of formula I are salts formed with inorganic acids, for example hydrohalic acids such as hydrochloric acid or hydrobromic acid, sulphuric acid, nitric acid, phosphoric acid etc, or with organic acids, for example acetic acid, citric acid, maleic acid, fumaric acid, tartaric acid, methanesulphonic acid, p-toluenesulphonic acid etc.

According to the process provided by the present invention, the compounds of formula I hereinbefore and their pharmaceutically acceptable acid addition salts are manufactured by (a) reacting 2-[(3(S)-amino-2(R)-hydroxy-4-phenylbutyl]-N-tert.butyl-decahydro-(4aS,8aS)-isoquinoline-3(S)-carboxamide having the formula

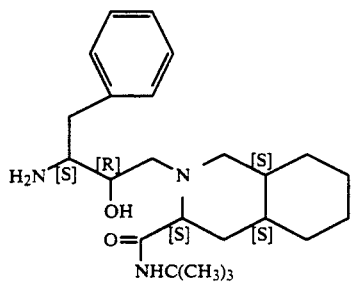

II with an acid having the formula

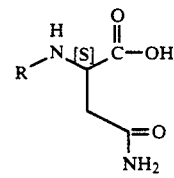

III wherein R is as defined above, or a reactive derivative thereof, or (b) reducing a compound having the formula

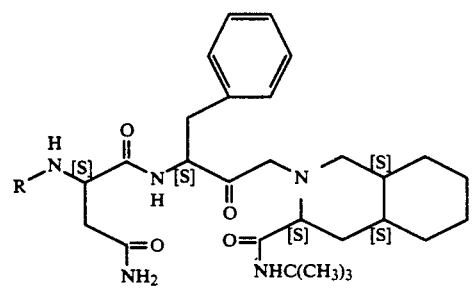

IV wherein R is as defined above,
and separating the desired 2 (R)-hydroxy isomer from the mixture obtained, or (c) reacting 2-[3(S)-[(L-asparaginyl)amino]-2(R)-hydroxy-4-phenylbutyl]-N-tert.butyl-decahydro-(4aS,8aS)-isoquinoline-3(S)-carboxamide having the formula

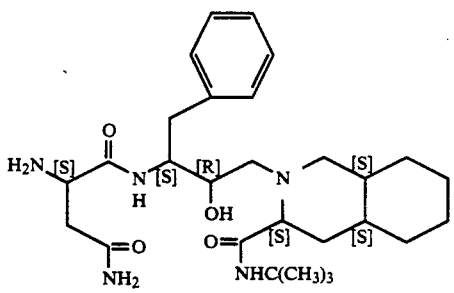

with an agent yielding the benzyloxycarbonyl or 2-quinolylcarbonyl group, and (d) if desired, converting a compound of formula I obtained into a pharmaceutically acceptable acid addition salt.

The reaction of a compound of formula II with an acid of formula III in accordance with embodiment (a) of the process can be carried out in accordance with methods well known in peptide chemistry. Thus, when an acid of formula III is used, the reaction is preferably carried out in the presence of a condensation agent such as hydroxybenzotriazole and dicyclohexylcarbodiimide. This reaction is conveniently carried out in an inert organic solvent such as an ether (for example, diethyl ether, tetrahydrofuran etc) or dimethylformamide at a low temperature, suitably at about −10° C. to +5° C. and especially at about 0° C. Suitable reactive derivatives of acids of formula III which can be used are, for example, the corresponding acid halides (for example, acid chlorides), acid anhydrides, mixed anhydrides, activated esters etc. When a reactive derivative is used, the reaction is conveniently carried out in an inert organic solvent such as a halogenated aliphatic hydrocarbon (for example, dichloromethane etc) or an ether (for example, diethyl ether, tetrahydrofuran etc) and, where appropriate, in the presence or an organic base (for example, N-ethylmorpholine, diisopropylethylamine etc) at a low temperature, suitably at about −10° C. to +5° C. and especially at about 0° C.

The reduction of a compound of formula IV in accordance with embodiment (b) of the process can be carried out according to methods well known in the art for the reduction of a carbonyl group to a hydroxy group. Thus, for example, the reduction can be carried out using a complex metal hydride such as an alkali metal borohydride, especially sodium borohydride, in an appropriate organic solvent such as an alkanol (for example, methanol, ethanol, propanol, isopropanol etc). Conveniently, the reduction is carried out at about room temperature (about 20° C.). The separation of the desired 2(R)-hydroxy isomer from the mixture obtained can be performed according to conventional methods, for example, by chromatography and the like.

In accordance with embodiment (c) of the process, the suitable agent yielding the benzyloxycarbonyl group is benzyl chloroformate. Suitable agents which yield the 2-quinolylcarbonyl group are the corresponding acid or reactive derivatives thereof such as the corresponding acid halides (for example, acid chloride), acid anhydride, mixed anhydrides, activated esters etc. The reaction of a compound of formula V with the aforementioned agents is carried out in the same manner as that described earlier in connection with embodiment (a) of the process.

The conversion of a compound of formula I into a pharmaceutically acceptable acid addition salt in accordance with embodiment (d) of the process can be carried out by treating such a compound in a conventional manner with an inorganic acid, for example a hydrohalic acid such as hydrochloric acid or hydrobromic acid, sulphuric acid, nitric acid, phosphoric acid etc, or with an organic acid such as acetic acid, citric acid, maleic acid, fumaric acid, tartaric acid, methanesulphonic acid, p-toluenesulphonic acid etc.

The compound of formula II which is used as starting material in embodiment (a) of the process is novel and also forms an object of the present invention.

The compound of formula II can be prepared, for example, by reacting a compound having the formula

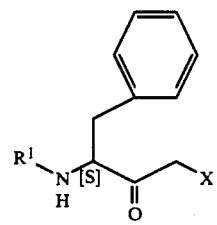

wherein R¹ is a amino-protecting group and X is a chlorine or bromine atom, with N-tert.butyl-decahydro-(4aS,8aS)isoquinoline-3(S)-carboxamide having the formula

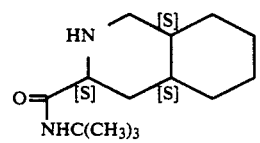

and reducing the resulting compound having the formula

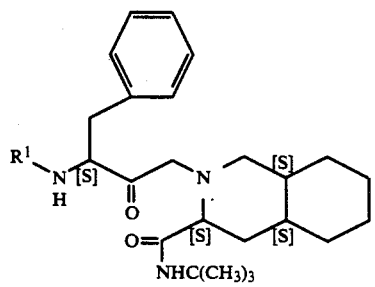

wherein R¹ is as defined above, separating the desired 2(R)-hydroxy isomer from the mixture obtained and cleaving off the group R¹ from the resulting compound having the formula

IX

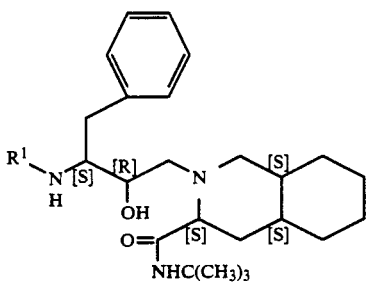

wherein $R^1$ is as defined above,
to give a compound of formula II.

The term "amino-protecting group" represents those amino-protecting groups commonly used and well known in the art of peptide chemistry, such as t-butoxycarbonyl or benzyloxycarbonyl.

The reaction of a compound of formula VI, preferably one in which $R^1$ is benzyloxycarbonyl, with a compound of formula VII can be carried out in a known manner; for example, in an inert organic solvent such as a halogenated aliphatic hydrocarbon (for example, dichloromethane etc) and in the presence of a base (for example, a trialkylamine such as triethylamine etc), conveniently at about room temperature (about 20° C.).

The reduction of a compound of formula VIII to give a compound of formula IX and the subsequent separation of the desired 2(R)-hydroxy isomer can be carried out as described earlier in connection with embodiment (b) of the process of the invention, that is, the reduction of a compound of formula IV and the separation of the desired 2(R)-hydroxy isomer from the mixture obtained.

The cleavage of the group $R^1$ from a compound of formula IX can also be carried out in a known manner; for example, using a strong inorganic acid such as a hydrohalic acid or a strong organic acid (for example, trifluoroacetic acid etc), conveniently at about 0° C. to about room temperature (about 20° C.). Alternatively, a hydrogenolytically-cleavable amino-protecting group $R^1$ can be cleaved off using hydrogen in the presence of a noble-metal catalyst (for example, a palladium catalyst such as palladium-on-carbon) in an organic solvent or solvent mixture which is inert under the reaction conditions (for example, an alkanol such as ethanol, isopropanol etc, an alkanecarboxylic acid ester such as ethyl acetate, etc) and conveniently at about room temperature (about 20° C.).

A further method for the preparation of the compound of formula II comprises firstly reacting a compound having the formula

X

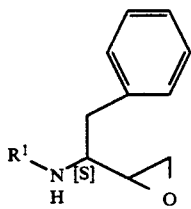

wherein $R^1$ is as defined above,
with the compound of formula VII hereinbefore, conveniently in an inert organic solvent such as an alkanol (for example, methanol etc), dimethylformamide or the like and at an elevated temperature, conveniently at about 60° C. to about 120° C., and then cleaving off the group $R^1$ in the reaction product (a compound of formula IX hereinbefore) as described earlier.

The compounds of formula IV which are used as starting materials in embodiment (b) of the process can be prepared, for example, by cleaving off the amino-protecting group $R^1$ from a compound of formula VIII and reacting the product with an acid of formula III or a reactive derivative thereof. This reaction can be carried out in an analogous manner to that described earlier in connection with embodiment (a) of the process.

The compound of formula V which is used as starting material in embodiments (c) of the process is novel and forms a further object of the present invention.

The compound of formula V can be prepared, for example, by cleaving off the benzyloxycarbonyl group R from the compound of formula I in which R represents benzyloxycarbonyl or the tert.butoxycarbonyl group form a compound corresponding to formula I but in which R represents tert.butoxycarbonyl. This latter compound can be prepared, for example, by reacting the compound of formula II with N-(tert.butoxycarbonyl)-L-asparagine in accordance with embodiment (a) of the process. The above cleavage is carried out in a manner analogous to that described earlier in connection with the cleavage of the group $R^1$ from a compound of formula VIII.

The starting materials of formula III and their reactive derivatives as well as the compounds of formulae VI, VII and X hereinbefore, insofar as they are not known compounds or analogues of known compounds, can be prepared in a similar manner to the known compounds or as described in the Examples hereinafter or in analogy thereto. Moreover, the agents used in embodiment (c) of the process are generally known compounds.

As mentioned earlier, the compounds of formula I and their pharmaceutically acceptable acid addition salts inhibit proteases of viral origin and are useful in the treatment or prophylaxis of viral infections, particularly of infections caused by HIV and other retroviruses in mammals, humans or non-humans.

The in vitro inhibition of HIV protease by the compounds provided by the present invention can be demonstrated by means of the following test:

HIV protease was expressed in E. coli and partially purified from soluble extracts of the bacterium by ammonium sulphate fractionation (0–30%). Protease activity was assayed using the protected hexapeptide succinyl-Ser-Leu-Asn-Tyr-Pro-Ile isobutylamide ($S^1$) or the protected heptapeptide succinyl-Val-Ser-Gln-Asn-Phe-Pro-Ile isobutylamide ($S^2$) as the substrate. Cleavage of the substrate was quantified by measuring the production of H-Pro-Ile isobutylamide by the spectrophotometric assay of N-terminal proline.

1.25 mM of substrate were dissolved in 125 mM of citrate buffer (pH 5.5) containing 0.125 mg/ml of Tween 20. 10 µl of a solution of various concentrations of the test compound (dissolved in methanol or dimethyl sulphoxide and diluted with water containing 0.1% Tween 20) and 10 µl of protease were added to 80 µl of the above buffered substrate. Digestion was carried out at 37° C. for a fixed period of time and was terminated by the addition of 1 ml of color reagent [30 µg/ml of isatin and 1.5 mg/ml of 2-(4-chlorobenzoyl)-benzoic acid in 10% acetone in ethanol (vol./vol.)]. The solution was heated in a water bath and then the pigmented residues were re-dissolved in 1 ml of 1% pyrogallol in 33% water in acetone (wt./vol./vol.). The optical density of the solution was measured spectrophotometrically at 599 nm. The formation of H-Pro-Ile isobutylamide in the presence of the test compound was compared with controls and the concentration of test compound required to give 50% inhibition ($I_{50}$) was determined by means of a graph plotted from the various concentrations of test compound used.

The in vitro antiviral activity of the compounds of formula I can be demonstrated in the assay described below:

Activity against HIV

This assay uses HTLV-III (strain RF) grown in C8166 cells (a human CD4+ T lymphoblastoid line) using RPM1 1640 medium with bicarbonate buffer, antibiotics and 10% fetal bovine serum.

A suspension of cells is infected with ten times the $TCD_{50}$ of virus and adsorption allowed to proceed for 90 minutes at 37° C. The cells are washed three times with medium. The test is carried out in 6 ml tissue culture tubes, each tube containing $2 \times 10^5$ infected cells in 1.5 ml of medium. Test compounds are dissolved in either aqueous medium or dimethyl sulphoxide, according to solubility, and a 15 µl solution of the substance added. The cultures are incubated at 37° C. for 72 hours in a humidified atmosphere containing 5% carbon dioxide in air. The cultures are then centrifuged and an aliquot of the supernatant solubilized with Nonidet P40 and subjected to an antigen capture assay which uses a primary antiserum with particular reactivity against the viral protein 24 and a horseradish peroxidase detection system. Color generation is measured spectrophotometrically and plotted against the concentration of test substance. The concentration that produces 50% protection is determined. ($I_{50}$).

A cytotoxicity assay based on dye uptake and metabolism or radio-labelled amino acid incorporation is run alongside the above assay in order to determine antiviral selectivity.

The results obtained in the foregoing tests using the compounds of formula I as the test compound are complied in the following Table.

TABLE

| Compound I | $I_{50}$ | | |
|---|---|---|---|
| | Inhibition of HIV protease (µM) | | Activity against HIV |
| R | $S^1$ | $S^2$ | (nM) |
| Benzyloxycarbonyl | <0.024 | <0.0027 | 20 |
| 2-Quinolylcarbonyl | <0.033 | <0.00037 | 2 |

The compounds of formula I and their pharmaceutically acceptable acid addition salts can be used as medicaments (for example, in the form of pharmaceutical preparations). The pharmaceutical preparations can be administered enterally such as orally (for example, in the form of tablets, coated tablets, dragees, hard and soft gelatin capsules, solutions, emulsions or suspensions), nasally (for example, in the form of nasal sprays) or rectally (for example, in the form of suppositories). However, the administration can also be effected parenterally such as intramuscularly or intravenously (for example, in the form of injection solutions).

For the manufacture of unit dosage forms such as tablets, coated tablets, dragees and hard gelatin capsules the compounds of formula I and their pharmaceutically acceptable acid addition salts can be processed with pharmaceutically inert, inorganic or organic excipients. Lactose, maize starch or derivatives thereof, talc, stearic acid or its salts etc can be used, for example, as such excipients for tablets, dragees and hard gelatin capsules.

Suitable excipients for unit dosage forms of soft gelatin capsules are, for example, vegetable oils, waxes, fats, semi-solid and liquid polyols etc.

Suitable excipients for the manufacture of the respective unit dosage forms of solutions and syrups are, for example, water, polyols, saccharose, invert sugar, glucose etc.

Suitable excipients for unit dosage forms of injection solutions are, for example, water, alcohols, polyols, glycerol, vegetable oils etc.

Suitable excipients for unit dosage forms of suppositories are, for example, natural or hardened oils, waxes, fats, semi-liquid or liquid polyols etc.

Moreover, the pharmaceutical preparations can contain preserving agents, solubilizers, viscosity-increasing substances, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

In accordance with the invention the compounds of formula I and their pharmaceutically acceptable acid addition salts can be used in the treatment or prophylaxis of viral infections, particularly of retroviral infections. The dosage can vary within wide limits and will, of course, be fitted to the individual requirements of the patient to be treated in each particular case. In general, in the case of oral administration there should suffice a daily dosage of about 3 mg to about 3 g, preferably about 10 mg to about 1 g (for example, approximately 300 mg per person), divided in preferably 1–3 unit doses, which can, for example, be of the same amount. It will, however, be appreciated that the upper limit given above can be exceeded when this is found to be indicated.

The following Examples illustrate the present invention in more detail. They are, however, not intended to limit its scope in any manner. Unless otherwise indicated, temperature is in degrees celsius. Unless otherwise indicated, examples were carried out as set forth below. Ratios are volume to volume.

EXAMPLE 1

A solution of 561 mg of 2-[3(S)-amino-2(R)-hydroxy-4-phenylbutyl]-N-tert.butyl-decahydro-(4aS,8aS)-isoquinoline-3(S)-carboxamide and 372 mg of N-(benzyloxycarbonyl)-L-asparagine in 20 ml of dry tetrahydrofuran was cooled in an ice/salt mixture. 189 mg of hydroxybenzotriazole, 161 mg of N-ethylmorpholine and 317 mg of dicyclohexylcarbodiimide were added and the mixture was stirred for 16 hours. The mixture was then diluted with ethyl acetate and filtered. The filtrate was washed with aqueous sodium bicarbonate solution and sodium chloride solution. The solvent was removed by evaporation and the residue was chromatographed on silica gel using dichloromethane/methanol (9:1) for the elution to give 434 mg of 2-[3(S)-[[N-(benzyloxycarbonyl)-L-asparaginyl]amino]-2(R)-hydroxy-4-phenylbutyl]-N-tert.butyl-decahydro-(4aS,8aS)-isoquinoline-3(S)-carboxamide as a white solid from methanol/diethyl ether; MS: m/e 650 [M+H]+, NMR: δ (d$_4$ CH$_3$OH, 400 MHz):

7.33 (5H, m, PhCH$_2$O), 7.25 (2H, m), 7.18 (2H, m), 7.09 (1H, m), 5.05 (2H, s, PhCH$_2$O), 4.42 (1H, dd, Asn α J=7.8, 6.1), 4.22 (1H, m, —CH$_2$CHCH(OH)— J=10.7, about 4), 3.85 (1H, m, —CHCH(OH)CH$_2$— J=8.0, 6.2, about 4), 3.02 (1H, dd, PhCH(H)CHJ= −13.9, about 4), 3.02 (1H, dd, 1$_{eq}$ J= −12.0, small), 2.69 (1H, dd, PhCH(H)CH— J= −13.9, 10.7), 2.63 (1H, dd, —CH(OH)CH(H)N— J= −12.6, 8.0), 2.62 (1H, dd, H3$_{ax}$ J=about 11, small), 2.57 (1H, dd, Asn β$_1$ J= −15.2, 6.1), 2.38 (1H, dd, Asn β$_2$ J= −15.2, 7.8), 2.19 (1H, dd, —CH(OH)CH(H)N— J= −12.6, 6.2), 2.17 (1H, dd, 1$_{ax}$ J= −12.0, 3.2), 2.07 (1H, m, H4$_{ax}$ J= −12.7, about 11, about 11.5), 1.78 (1H, m, H4a J$_{4a-4ax}$=about 11.5, J$_{4a-4eq}$=small, J$_{4a-8a}$=small), 1.63 (1H, m, H8a J$_{8a-1ax}$=3.2, J$_{8a-1eq}$=small, J$_{8a-4a}$=small), 1.35 (1H, m, H4$_{eq}$ J= −12.7, small, small), 1.30 (9H, s, t-butyl), 2.0–1.2 (8H, m).

The 2-[3(S)-amino-2(R)-hydroxy-4-phenylbutyl]-N-tert.butyl-decahydro-(4aS,8aS)-isoquinoline-3(S)-carboxamide used as the starting material was prepared as follows: (i) A suspension of 12.676 g (71.6 mmol) of 1,2,3,4-tetrahydro-3(S)-isoquinolinecarboxylic acid (Chem. Pharm. Bull. 1983, 31, 312) in 200 ml of 90% acetic acid was hydrogenated at 80° C. and under 140 atmospheres pressure over 5% rhodium-on-carbon for 24 hours. The mixture was left to cool to room temperature and the catalyst was then filtered off. The filtrate was evaporated to give a gum which was dissolved in 10 ml of ethyl acetate and added slowly to 100 ml of vigorously stirred diisopropyl ether. A resinous precipitate was produced. The supernatant liquors were removed by decantation and the precipitate was extracted with hot ethyl acetate. This hot solution was poured into a vigorously stirred mixture of 150 ml of diethyl ether/diisopropyl ether (1:1) to give a pale grey solid which was collected by filtration, washed with diethyl ether and dried. There were obtained 5.209 g of a mixture of decahydroisoquinoline-3(S)-carboxylic acids consisting of predominantly (about 65%) the 4aS,8aS isomer together with the 4aR,8aR isomer (about 25%) and about 10% of the trans isomers; MS: m/e 184 [M+H]$^+$.

(ii) 9.036 g (49.4 mmol) of the foregoing mixture of decahydroisoquinoline-3(S)-carboxylic acids were dissolved in 50 ml (50 mmol) of 1M sodium hydroxide solution and the resulting solution was cooled to 0° C. 7.40 ml (51.87 mmol) of benzyl chloroformate and 58.7 ml (58.7 mmol) of 1M sodium hydroxide solution were added dropwise over a period of 1 hour while maintaining a temperature of 0°-5° C. by cooling. The mixture was then stirred for a further 2 hours, during which time the mixture was allowed to warm to room temperature. 100 ml of diethyl ether were added and the mixture was filtered, whereby the insoluble R,R-isomer was removed. The aqueous layer of the filtrate was separated and adjusted to pH 1.5–2 by the addition of concentrated hydrochloric acid, whereby an oil precipitated. The mixture was extracted twice with 100 ml of ethyl acetate each time. The combined organic extracts were washed with water, dried over anhydrous sodium sulphate and evaporated to give an oil. This oil was dissolved in 35 ml of ethyl acetate and 2.85 ml (25 mmol) of cyclohexylamine were added. The white precipitate was collected by filtration to give, after several fractional recrystallizations from methanol/ethyl acetate, 2.38 g of the cyclohexylamine salt of 2-(benzyloxycarbonyl)-decahydro-(4aS,8aS)-isoquinoline-3(S)-carboxylic acid; MS: m/e 318 [M+H]$^+$.

(iii) 2.334 g of the cyclohexylamine salt of 2-benzyloxycarbonyl)-decahydro-(4aS,8aS)-isoquinoline-3(S)-carboxylic acid were partitioned between 50 ml of ethyl acetate and 50 ml of 10% citric acid solution. The organic phase was separated, washed with water, filtered and evaporated to give 1.87 g of 2-(benzyloxycarbonyl)-decahydro-(4aS,8aS)-isoquinoline-3(S)-carboxylic acid in the form of a colorless gum; MS: m/e 318 [M+H]$^+$.

(iv) A solution of 0.634 g (2.0 mmol) of 2-(benzyloxycarbonyl)-decahydro-(4aS,8aS)-isoquinoline-3(S)-carboxylic acid in 6 ml of dimethoxyethane was treated with 0.23 g (2.0 mmol) of N-hydroxysuccinimide and 0.412 g (2.0 mmol) of dicyclohexylcarbodiimide. The mixture was stirred at room temperature for 18 hours. The mixture was filtered and the filtrate was evaporated to give 0.879 g of the N-hydroxysuccinimide ester of the foregoing acid in the form of a pale yellow oil. A solution of 0.828 g (2.0 mmol) of the foregoing N-hydroxysuccinimide ester in 5 ml of dichloromethane was stirred, cooled to 0° C. and treated with 0.219 g (3.0 mmol) of tert.butylamine. The mixture was stirred at 0° C. for 2 hours and then at room temperature for 4.5 hours. The mixture was then washed with 2M hydrochloric acid, sodium carbonate solution and sodium chloride solution, dried over anhydrous magnesium sulphate and evaporated. The residue was dissolved in 20 ml of diethyl ether and filtered. The filtrate was evaporated to give 0.712 g of 2-(benzyloxycarbonyl)-N-tert.butyl-decahydro-(4aS,8aS)-isoquinoline-3(S)-carboxamide in the form of a white solid; MS: m/e 373 [M+H]$^+$.

(v) A solution of 0.689 g (1.85 mmol) of 2-benzyloxycarbonyl)-N-tert.butyl-decahydro-(4aS,8aS)-isoquinoline-3(S)-carboxamide in 20 ml of ethanol was hydrogenated in the presence of 0.01 g of 10% palladium-on-carbon at room temperature and under atmospheric pressure for 18 hours. The catalyst was removed by filtration and the solvent was removed by evaporation to give in quantitative yield N-tert.butyl-decahydro-(4aS,8aS)-isoquinoline-3(S)-carboxamide as a clear oil; MS: m/e 239 [M+H]$^+$, which was used in the next step without further purification.

(vi) A solution of 440 mg of N-tert.butyl-decahydro-(4aS,8aS)-isoquinoline-3(S)-carboxamide and 549 mg of 3(S)-(benzyloxyformamido)-1,2(S)-epoxy-4-phenylbutane in 6 ml of ethanol was stirred at 60° C. for 7 hours. A further 54 mg of 3(S)-(benzyloxyformamido)-1,2(S)-epoxy-4-phenylbutane were added and the solution was stirred at 20° C. for 16 hours. The solvent was removed by evaporation and the residue was chromatographed on silica gel using diethyl ether/n-hexane/methanol (47.5:47.5:5) for the elution to give 771 mg of 2-[3(S)-(benzyloxyformamido)-2(R)-hydroxy-4-phenylbutyl-N-tert.butyl-decahydro-(4aS,8aS)-isoquinoline-3(S)-carboxamide as a white solid; MS: m/e 536 [M+H]$^+$.

(vii) A solution of 747 mg of 2-[3(S)-(benzyloxyformamido)-2(R)-hydroxy-4-phenylbutyl-N-tert.butyl-decahydro-(4aS,8aS)-isoquinoline-3(S)-carboxamide in 40 ml of ethanol was hydrogenated over 10% palladium-on-carbon at 20° C. and under atmospheric pressure for 5 hours. The catalyst was removed by filtration and the filtrate was evaporated to give 561 mg of 2-[3(S)-amino-2(R)-hydroxy-4-phenylbutyl]-N-tert.butyl-decahydro-(4aS,8aS)-isoquinoline-3(S)-carboxamide as a buff colored solid.

EXAMPLE 2

A solution of 154 mg of 2-[3(S)-[(L-asparaginyl)amino]-2(R)-hydroxy-4-phenylbutyl]-N-tert.butyl-decahydro(4aS,8aS)-isoquinoline-3(S)-carboxamide and 52 mg of quinaldic acid in 6 ml of dry tetrahydrofuran was cooled in an ice/salt mixture. 41 mg of hydroxybenzotriazole, 35 mg of N-ethylmorpholine and 68 mg of dicyclohexylcarbodiimide were added and the mixture was stirred for 64 hours. The mixture was diluted with ethyl acetate and filtered. The filtrate was washed with aqueous sodium bicarbonate solution and with sodium chloride solution and then evaporated. The residue was chromatographed on silica gel using dichloromethane/methanol (9:1) for the elution to give 50 mg of N-tert.butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide as a white solid; MS: m/e 671 [M+H]+, NMR: δ (d4 CH3OH, 400 MHz):

8.52 (1H, m), 8.18 (1H, m), 8.14 (1H, m), 8.02 (1H, m), 7.84 (1H, m), 7.69 (1H, m), 7.18 (2H, m), 6.90 (2H, m), 6.72 (1H, m), 4.93 (1H, dd, Asn αCH J=6.6, 6.8), 4.27 (1H, m, —CH2CHCH(OH)— J=3.8, 3.8, 11.0), 3.89 (1H, m, —CHCH(OH)CH2— J=7.2, 6.4, 3.8), 3.06 (1H, dd, H1$_{eq}$ J=−12.0, 3.0), 3.02 (1H, dd, PhCH(H)CH— J=−14.0, 3.8), 2.77 (1H, dd, Asn β1 J=−15.6, 6.6), 2.68 (1H, dd, Asn β2 J=−15.6, 6.8), 2.68 (1H, dd, PhCH(H)CH— J=−14.0, 11.0), about 2.68 (1H, dd, —CH(OH)CH(H)CH— J=−12.0, 7.2), 2.63 (1H, dd, H3$_{ax}$ J=11.0, 2.2), 2.22 (1H, dd, —CH(OH)CH(H)N— J=−12.0, 6.4), 2.18 (1H, dd, H1$_{ax}$ J=−12.0, 2.2), 2.06 (1H, m, H4$_{ax}$ J=−11.0, 11.0), 1.78 (1H, m, 4a J$_{4a-4ax}$=11.0, J$_{4a-4eq}$=about 4, J$_{4a-8a}$=about 4), 1.65 (1H, m, 8a J$_{8a-1ax}$=2.2 J$_{8a-1eq}$=3.0 J$_{8a-4a}$=about 4), 1.37 (1H, m, H4$_{eq}$ J= −11.0, 2.2, about 4), 1.30 (9H, s, t-butyl), 2.0–1.2 (8H, m).

The 2-[3(S)-[(L-asparaginyl)amino]-2(R)-hydroxy-4-phenylbutyl]-N-tert.butyl-decahydro-(4aS,8aS)-isoquinoline-3(S)-carboxamide used as the starting material was prepared as follows:

A solution of 195 mg of 2-[3(S)-[[N-(benzyloxycarbonyl)-L-asparaginyl]amino]-2(R)-hydroxy-4-phenylbutyl]-N-tert.butyl-decahydro-(4aS,8aS)-isoquinoline-3(S)-carboxamide in 20 ml of ethanol was hydrogenated at room temperature and atmospheric pressure for 18 hours over 10 mg of 10% palladium-on-charcoal. The catalyst was filtered off and the filtrate was evaporated under reduced pressure to give 154 mg of 2-[3(S)-[(L-asparaginyl)amino]2(R)-hydroxy-4-phenylbutyl]-N-tert.butyl-decahydro-(4aS,8aS)-isoquinoline-3(S)-carboxamide.

EXAMPLE 3

A solution of 287 mg of N-(2-quinolylcarbonyl)-L-asparagine and 401 mg of 2-[3(S)-amino-2(R)-hydroxy-4-phenylbutyl]-N-tert.butyl-decahydro-(4aS,8aS)-isoquinoline-3(S)-carboxamide [prepared as described in Example 1 (i)-(vii)] in 3 ml of tetrahydrofuran was cooled to −10° C. and 163 mg of 3-hydroxy-1,2,3-benzotriazin-4(3H)-one and 220 mg of dicyclohexylcarbodiimide were added. The mixture was stirred at −10° C. for 2 hours and at 20° C. for 16 hours, then diluted with ethyl acetate and filtered. The filtrate was washed with saturated sodium bicarbonate solution and saturated sodium chloride solution and then evaporated. The residue was chromatographed on silica gel using 4% (by volume) methanol in dichloromethane for the elution to give 537 mg of N-tert.butyl-decahydro-2[2(R)-hydroxy-4-phenyl-3-(S)-[[N-(2-quinolylcarbonyl)-L-asparaginyl]amino]butyl]-(4aS,8aS)-isoquinoline-3(S)-carboxamide which was identical with the product obtained in the first paragraph of Example 2.

The N-(2-quinolylcarbonyl)-L-asparagine used as the starting material was prepared as follows:

A mixture of 540 mg of quinaldic acid succinimide ester and 300 mg of L-asparagine monohydrate in 2 ml of dimethylformamide was stirred at 20° C. for 96 hours. The solvent was removed by evaporation to give a white solid residue which was stirred vigorously in 10 ml of dichloromethane, filtered off and washed with dichloromethane. There were thus obtained 431 mg of N-(2-quinolylcarbonyl)-L-asparagine as a white solid; MS: m/e 288[M+H]+.

The following Example illustrates the manufacture of a pharmaceutical preparation containing a compound of formula I or a pharmaceutically acceptable acid addition salt thereof as the active ingredient:

EXAMPLE A

An aqueous solution of the active ingredient is filtered sterile and mixed while warming with a sterile gelatin solution, which contains phenol as a preserving agent, using amounts such that 1.00 ml of the resulting solution contains 3.0 mg of active ingredient, 150.0 mg of gelatin, 4.7 mg of phenol and distilled water ad 1.0 ml. The mixture is filled into vials of 1.0 ml capacity under aseptic conditions.

We claim:

1. A compound having the formula

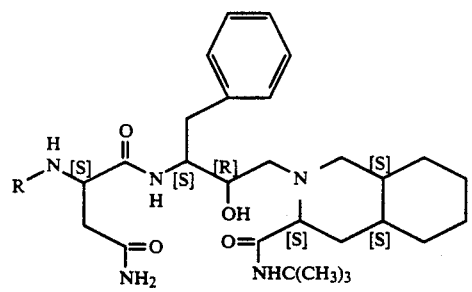

I wherein R is benzyloxycarbonyl or 2-quinolylcarbonyl, and its pharmaceutically acceptable acid addition salts.

2. The compound of claim 1, N-tert.butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide.

3. The compound of claim 1, N-tert.butyl-decahydro-2-[2(R)-hydroxy-4-phenyl-3(S)-[[N-benzyloxycarbonyl)-L-asparaginyl]amino]butyl]-(4aS,8aS)-isoquinoline-3(S)-carboxamide.

4. A compound having the formula

II

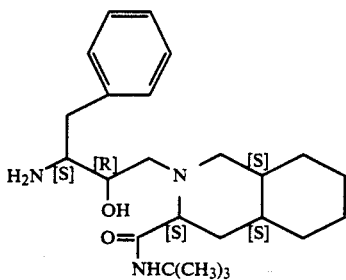

5. A compound having the formula

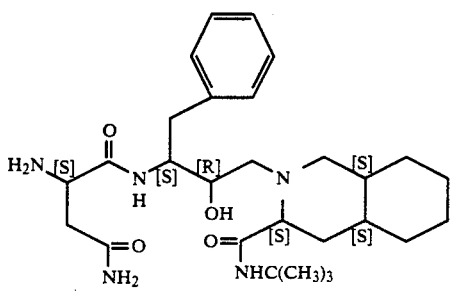

6. A pharmaceutical composition which comprises a therapeutically effective amount of a compound having the formula

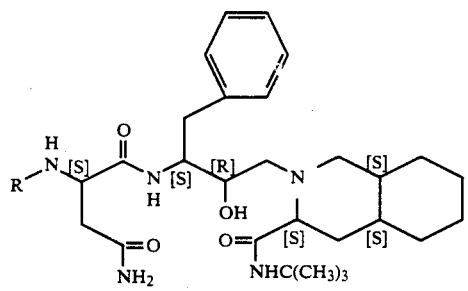

wherein R is benzyloxycarbonyl or 2-quinolylcarbonyl,
or a pharmaceutically acceptable acid addition salt thereof, and a therapeutically inert carrier.

7. The pharmaceutical composition of claim 6 wherein in formula I, R is benzyloxycarbonyl.

8. The pharmaceutical composition of claim 6, wherein in formula I, R is 2-quinolylcarbonyl.

9. The pharmaceutical composition of claim 6, which is present in an amount effective to control viral infections.

10. The pharmaceutical composition of claim 6, wherein the amount of said compound of formula I is from about 3 mg to about 3000 mg.

11. The pharmaceutical composition of claim 10, wherein the amount of said compound of formula I is from about 10 mg to about 1000 mg.

12. The pharmaceutical composition of claim 6 which is in unit dosage form.

13. The pharmaceutical composition of claim 12 wherein the amount of compound of formula I is from about 10 mg to about 1000 mg.

14. The pharmaceutical composition of claim 12 wherein said unit dosage form is selected from the group consisting of tablets, coated tablets, dragees, hard gelatin capsules, soft gelatin capsules, solutions, emulsions, suspensions, syrups, sprays, and suppositories.

15. A method for treating a mammal having viral infections, which comprises administering to said mammal a compound having the formula

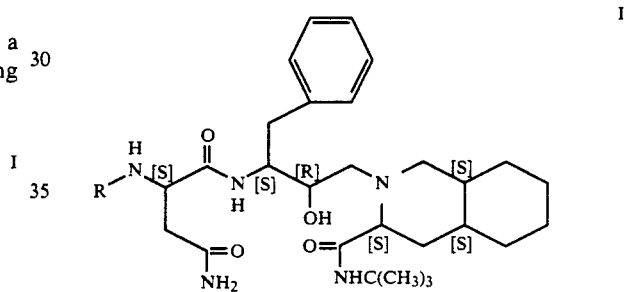

wherein R is benzyloxycarbonyl or 2-quinolylcarbonyl,
or a pharmaceutically acceptable acid addition salt thereof in an amount which is effective in treating viral infections.

16. The method of claim 15 wherein, in formula I R is benzyloxycarbonyl.

17. The method of claim 15 wherein, in formula I R is 2-quinolylcarbonyl.

* * * * *